US010146326B2

(12) United States Patent  
Griffin et al.

(10) Patent No.: US 10,146,326 B2  
(45) Date of Patent: *Dec. 4, 2018

(54) METHOD AND HANDHELD ELECTRONIC DEVICE FOR DISPLAYING AND SELECTING DIACRITICS

(71) Applicant: BlackBerry Limited, Waterloo (CA)

(72) Inventors: Jason Tyler Griffin, Kitchener (CA); Michael George Langlois, Almonte (CA); John Jong-Suk Lee, Waterloo (CA); Alen Mujkic, Mississauga (CA); Andrew Douglas Bocking, Conestogo (CA); Parul Nanda Gilani, Mississauga (CA)

(73) Assignee: BlackBerry Limited, Waterloo, Ontario (CA)

(*) Notice: Subject to any disclaimer, the term of this patent is extended or adjusted under 35 U.S.C. 154(b) by 80 days.

This patent is subject to a terminal disclaimer.

(21) Appl. No.: 14/949,202

(22) Filed: Nov. 23, 2015

(65) Prior Publication Data

US 2016/0077602 A1    Mar. 17, 2016

Related U.S. Application Data

(63) Continuation of application No. 13/614,375, filed on Sep. 13, 2012, now Pat. No. 9,195,318, which is a  
(Continued)

(51) Int. Cl.  
G06F 3/048    (2013.01)  
G06F 3/023    (2006.01)  
(Continued)

(52) U.S. Cl.  
CPC .......... *G06F 3/0236* (2013.01); *G06F 1/1662* (2013.01); *G06F 3/041* (2013.01); *G06F 1/1615* (2013.01); *G06F 19/3456* (2013.01)

(58) Field of Classification Search  
CPC .............. G06F 17/2223; G06F 17/273; G06F 17/2735; G06F 17/289  
See application file for complete search history.

(56) References Cited

U.S. PATENT DOCUMENTS 5,893,133 A * 4/1999 Chen ................... G06F 17/2863  
                                                      400/110  
5,953,541 A * 9/1999 King .................... G06F 3/0238  
                                                      710/67

(Continued)

FOREIGN PATENT DOCUMENTS

EP          1271295        1/2003  
WO       2007037809        4/2007

OTHER PUBLICATIONS

FitalyStamp for the Palm Organizer, version 1; user's manual, Textware Solution, 1998-2000, 16 pages.

(Continued)

*Primary Examiner* — Linh K Pham  
(74) *Attorney, Agent, or Firm* — Fish & Richardson P.C.

(57) ABSTRACT

A handheld electronic device includes a keypad having a plurality of keys and a selection member; a display component; and a processor cooperating with the keypad and the display component to provide a display at the display component. The display includes a first representation of a plurality of the keys, and at least one of: (a) a second representation of an activated one of the input members, (b) a third representation including a plurality of diacritics disposed about an activated one of the input members, and (c) a fourth representation including a plurality of diacritics disposed about an activated one of the input members, and a direction of selection between the activated one of the input members and one of the diacritics. The processor cooperates with the selection member to adjust the direction (Continued)

of selection, and select one of the diacritics for display by the display component.

20 Claims, 5 Drawing Sheets

Related U.S. Application Data continuation of application No. 12/354,091, filed on Jan. 15, 2009, now Pat. No. 8,296,680.

(51) Int. Cl.
*G06F 1/16* (2006.01)
*G06F 3/041* (2006.01)
*G06F 19/00* (2018.01)

(56) References Cited

U.S. PATENT DOCUMENTS

| | | | |
|---|---|---|---|
| 6,286,064 | B1 | 9/2001 | King et al. |
| 7,098,896 | B2 | 8/2006 | Kushler et al. |
| 8,035,534 | B2 | 10/2011 | Scott |
| 8,184,022 | B2 | 5/2012 | Scott |
| 8,296,680 | B2 | 10/2012 | Griffin |
| 2003/0014239 | A1 | 1/2003 | Ichbiah et al. |
| 2003/0064736 | A1* | 4/2003 | Bickerton ............ G06F 3/0233 455/466 |
| 2004/0140956 | A1 | 7/2004 | Kushler et al. |
| 2005/0223308 | A1 | 10/2005 | Gunn et al. |
| 2006/0053387 | A1* | 3/2006 | Ording ............ G06F 3/04883 715/773 |
| 2007/0040813 | A1 | 2/2007 | Kushler et al. |
| 2007/0061753 | A1* | 3/2007 | Ng ............ G06F 3/0237 715/816 |
| 2007/0256026 | A1 | 11/2007 | Klassen et al. |
| 2008/0114590 | A1 | 5/2008 | Scott |
| 2008/0131031 | A1 | 6/2008 | Scott |
| 2009/0058823 | A1* | 3/2009 | Kocienda ............ G06F 3/0236 345/173 |
| 2011/0316789 | A1 | 12/2011 | Scott |
| 2012/0028687 | A1 | 2/2012 | Wykes et al. |
| 2012/0146955 | A1 | 6/2012 | Martin-Cocher et al. |
| 2012/0200505 | A1 | 8/2012 | Scott |
| 2013/0110503 | A1 | 5/2013 | Scott |

OTHER PUBLICATIONS

Per Ola Kristensson; Discrete and Continuous Shape Writing for Text Entry and Control; 2007; http://pokristensson.com/pubs/KristenssonDoctoralDissertation2007.pdf.

Textware Solutions et al., "Fitaly 4 User's Manual", XP-002529257, Dec. 20, 2007, 7 pp.

"iPhone Tips: typing accented characters," pqdvd.com [online], archived on May 7, 2008. Retrieved from the Internet: <URL: https://web.archive.org/web/20080507053345/http://www.pqdvd.com/blog/iphone/iphone-tips-iphone-tips-typing-accented-characters/>, 3 pages.

Wikipedia, "Pie menu", Pie menu—Wikipedia, the free encyclopedia, http://en.wikipedia.org/wiki/Marking.sub.--menu, Oct. 8, 2008, 3 pp.

European Search Report and Written Opinion for App. No. EP09150666, dated Jun. 5, 2009, 5 pages.

\* cited by examiner

METHOD AND HANDHELD ELECTRONIC DEVICE FOR DISPLAYING AND SELECTING DIACRITICS

CROSS REFERENCE TO RELATED APPLICATIONS

This application is a continuation of U.S. application No. 13/614,375, filed on Sep. 13, 2012, now U.S. Pat. No. 9,195,318, which is a continuation of U.S. application No. 12/354,091, filed on Jan. 15, 2009, now U.S. Pat. No. 8,296,680, the entire contents of which are hereby expressly incorporated by reference herein in their entireties.

BACKGROUND

Field

The disclosed and claimed concept relates generally to handheld electronic devices and, more particularly, to handheld electronic devices and methods that display and select diacritics.

Description of the Related Art

Numerous types of handheld electronic devices are known. Examples of such handheld electronic devices include, for instance, personal data assistants (PDAs), handheld computers, two-way pagers, cellular telephones, and the like. Many handheld electronic devices also feature wireless communication capability, although many such handheld electronic devices are stand-alone devices that are functional without communication with other devices. Such handheld electronic devices are generally intended to be portable, and thus are of a relatively compact configuration in which keys and other input structures often perform a plurality of functions under certain circumstances or may otherwise have a plurality of aspects or features assigned thereto.

Some known handheld electronic devices including, for example, a track ball, insert accents from a horizontal menu or list in response to a user holding a key and scrolling across using the track ball. For example, in response to entry of the letter "e" (e.g., from either a reduced keypad or from a full keypad), a horizontal menu or list shows, for example, "ë", "ê", "è", "é" and "e". Alternatively, a menu or list is not employed, but scrolling simply changes the accents, with the user not being necessarily aware of the future sequence of different possible accents.

Another known method of accent insertion by a handheld electronic device is to list the accents in a secondary grid format for insertion in response to a minimum of two user clicks.

Often, when a user is attempting to enter an accented character, a break in fluid typing is required in known handheld electronic devices, since the user must often search through a list or grid of all accents in order to find the desired accent. Hence, some users often neglect to include accents or an obscure letter treatment due to the large break in fluid typing.

A pie menu (also known as a radial menu or marking menu) is a circular popup menu where selection depends on direction. A pie menu is made of several "pie slices" around an inactive center and works best with stylus input, and well with a mouse. Pie menus also work well with keyboard acceleration, particularly four and eight item menus, on the cursor keys and the number pad. A goal of pie menus is to provide a smooth, reliable gestural style of interaction for novices and experts. A slice can lead to another pie menu; selecting this may center the mouse cursor in the new menu. Pie menus are often context-sensitive, showing different options depending on what the mouse cursor was pointing at when the menu was requested. Pie menus are drawn as pie slices with a hole in the middle for an easy way to exit the menu.

There is room for improvement in handheld electronic devices that display and select diacritics.

There is also room for improvement in methods of displaying and selecting diacritics for a handheld electronic device.

BRIEF DESCRIPTION OF THE DRAWINGS

A full understanding of the disclosed and claimed concept can be gained from the following description of the preferred embodiments when read in conjunction with the accompanying drawings in which:

Similar numerals refer to similar parts throughout the specification.

DESCRIPTION

As employed herein, the term "number" shall mean one or an integer greater than one (i.e., a plurality).

As employed herein, the term "processor" means a programmable analog and/or digital device that can store, retrieve, and process data; a computer; a workstation; a personal computer; a microprocessor; a microcontroller; a microcomputer, a central processing unit; a mainframe computer; a mini-computer; a server; a networked processor; or any suitable processing device or apparatus.

As employed herein, the term "characters" means letters, digits, symbols and the like and can additionally include ideographic characters, components thereof, and the like.

As employed herein, the term "mark" means a displayed symbol (e.g., without limitation, as is employed for punctuation or pronunciation).

As employed herein, the terms "diacritical mark" and "diacritic" mean a mark added to a letter or other character to indicate a special pronunciation, or a mark near or through an orthographic, phonetic or other character, or a combination of characters, indicating a phonetic value different from that given to an unmarked or otherwise marked element. Some non-limiting examples of diacritical marks and diacritics include: (1) an accent or accent mark (e.g., " ´ " placed above the letter "e", thus "é", to provide an acute accent; "`" placed above the letter "e", thus "è" to provide a grave accent), which is a diacritical mark used to indicate stress or placed above a vowel to indicate a special pronunciation; (2) breve, which is a diacritical mark (e.g., U-shaped; placed over a vowel to indicate a relatively short sound; (3) cedilla, which is a diacritical mark (e.g., ",") placed below the letter "c" to indicate that it is pronounced as an "s"; (4) circumflex, a diacritical mark (e.g., "^") placed above a vowel in some languages to indicate a special phonetic quality; (5) hacek or wedge (e.g., V-shaped), which are diacritical, marks (e.g., an inverted circumflex) placed above certain letters (e.g., the letter "c") to indicate pronunciation; (6) macron, which is a diacritical mark (e.g., "–") placed above a vowel to indicate a relatively long sound; (7) tilde, which is a diacritical mark (e.g., "~") placed over the letter "n" in Spanish to indicate a palatal nasal sound or over a vowel in Portuguese to indicate nasalization; and (8) umlaut, dieresis, or diaeresis, which are diacritical marks (e.g., two dots or "¨") placed over it vowel in German to indicate a change in sound.

As employed herein, the term "reduced keypad" means a keypad or other suitable keyboard in which multiple letters, symbols, and/or digits, and the like, are assigned to any given key. For example and without limitation, a touch-tone telephone includes a reduced keypad by providing twelve keys, of which ten have digits thereon, and of these ten keys eight have Latin letters assigned thereto. For instance, one of the keys includes the digit "2" as well as the letters "A", "B", and "C". Other known reduced keypads have included other arrangements of keys, letters, symbols, digits, and the like. Since a single actuation of such a key potentially could be intended by the user to refer to any of the letters "A", "B", and, "C", and potentially could also be intended to refer to the digit "2", the input generally is an ambiguous input and is in need of some type of disambiguation in order to be useful for text entry purposes.

As employed herein, the term "full keypad" means a keypad or other suitable keyboard in which plural letters are not assigned to any given key. Optionally, some of the other keys may have multiple symbols and/or digits, and the like, assigned to each of those other keys.

As employed herein the term "touch pad" means an input apparatus structured using an suitable technology to determine the location of a user's finger (e.g., without limitation, X_Finger Y_Finger) with respect to two axes (e.g., without limitation, a horizontal axis and a vertical axis; an X axis and a Y axis) of a planar or generally planar surface.

Embodiments of the disclosed and claimed concept solve the problem of displaying possible diacritics and selecting one of those diacritics by employing, for example, a relatively quick directional indicator that preferably mimics the directional stroke of a diacritical mark, such as, for example, an accent. Preferably, the directional indicator employs both the proximity and the transfer of visual elements from the character employing the diacritical mark. This is very different from known accenting used interlaces of known handheld electronic devices.

In accordance with one aspect of the disclosed and claimed concept, a handheld electronic device comprises: an input component comprising a plurality of input members and a selection member; a display component; and a processor structured to cooperate with the input component and the display component to display at the display component: a first representation of a plurality of the plurality of input members, and at least one of: (a) a second representation of an activated one of the plurality of input members, (b) a third representation including a plurality of diacritics disposed about an activated one of the plurality of input members, and (c) fourth representation including a plurality of diacritics disposed about an activated one of the plurality of input members, and a direction of selection between the activated one of the plurality of input members and one of the plurality of diacritics, wherein the processor is further structured to cooperate with the selection member to adjust the direction of selection, and to select one of the plurality of diacritics for display by the display component.

The third representation may be a selection window displayed an the display component.

The selection window may include a representation of a portion of a keypad or touchpad as the first representation, and also the second representation and the fourth representation.

The fourth representation may be a direction of selection or spatial reference corresponding to the selected one of the plurality of diacritics.

The selection window may be a circular selection window having a center and a circular edge; the second representation may be disposed at about the center of the circular selection window; each of the plurality of diacritics may be disposed at a different position proximate the circular edge of the circular selection window; and the fourth representation may be disposed between the center of the circular selection window and the selected one of the plurality of diacritics.

In addition to the plurality of diacritics, the display component may display a number of marks, each of the number of marks haying a logical connection to a character represented by the second representation.

The display component may include a selection window having a representation of a portion of a keypad or touchpad, a designation of a selected character, and a direction of selection corresponding to the directionality of the selected one of the plurality of diacritics.

The selected one of the plurality of diacritics may not have a logical placement corresponding to a selected character represented by the second representation of the activated one of the plurality of input members.

In accordance with another aspect of the disclosed and claimed concept, a method of selecting diacritics is for a handheld electronic device including an input component having a plurality of input members and a selection member, a display component, and a processor cooperating with the input component and the display component. The method comprises: displaying a first representation of a plurality of the plurality of input members; displaying at least one of: (a) a second representation of an activated one of the plurality of input members, (b) a third representation including a plurality of diacritics disposed about an activated one of the plurality of input members, and (c) a fourth representation including a plurality of diacritics disposed about an activated one of the plurality of input members, and a direction of selection between the activated one of the plurality of input members and one of the plurality of diacritics; adjusting the direction of selection; selecting one of the plurality of diacritics; and displaying the selected one of the plurality of diacritics.

The method may further comprise displaying a selection window as the third representation, including with the selection window a center and an outside edge; disposing the second representation at about the center of the selection window; disposing each of the plurality of diacritics at a different position proximate the outside edge of the selection window; disposing the fourth representation between the center of the selection window and the selected one of the plurality of diacritics; representing a character with the second representation; and employing for a number of the plurality of diacritics and the different position thereof a logical connection to the character represented by the second representation.

The method may further comprise displaying a circular selection window having a center and a circular edge; disposing the second representation at about the center of the circular selection window; disposing each of the plurality of diacritics at a different position proximate the circular edge of the circular selection window; and disposing the fourth representation between the center of the circular selection window and the selected one of the plurality of diacritics.

In accordance with another aspect of the disclosed and claimed concept, a handheld electronic device comprises; a touchpad; a display component; and a processor structured to cooperate with the touchpad and the display component to display at the display component: a first representation of a plurality of input members, and at least one of: (a) a second representation of an activated one of the plurality of input members, and (b) a third representation including a plurality of diacritics disposed about an activated one of the plurality of input members, wherein the processor is further structured to cooperate with the touchpad to select one of the plurality of diacritics for display by the display component.

In accordance with another aspect of the disclosed and claimed concept, a method of selecting diacritics is for a handheld electronic device including a touchpad, a display component, and a processor cooperating with the touchpad and the display component. The method comprises: displaying a first representation of a plurality of input members; displaying at least one of: (a) a second representation of an activated one of the plurality of input members, and (b) a third representation including a plurality of diacritics disposed about an activated one of the plurality of input members; selecting one of the plurality of diacritics responsive to the touchpad; and displaying the selected one of the plurality of diacritics.

Figure 1:
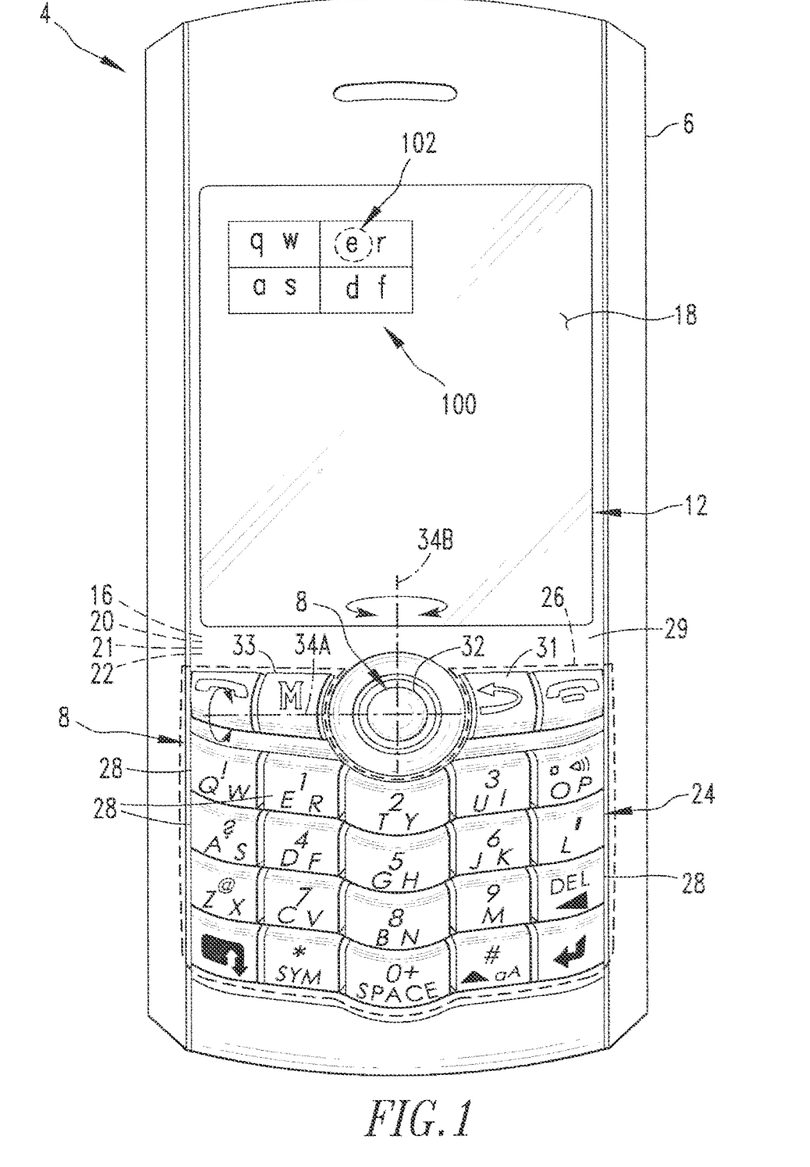
FIG. 1 is a top plan view of a handheld electronic device in accordance with embodiments of the disclosed and claimed concept.
Figure 1A:
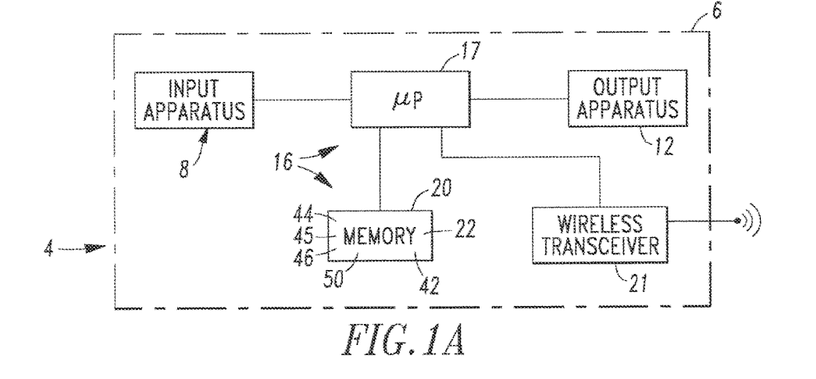
FIG. 1A is a block diagram in schematic form of the handheld electronic device of FIG. 1.

An improved handheld electronic device 4 is indicated generally in FIG. 1 and is depicted schematically in FIG. 1A. The example handheld electronic device 4 includes a housing 6 upon which are disposed an input apparatus 8, an output apparatus 12, and a processor apparatus 16. The input apparatus 8 is structured to provide input to the processor apparatus 16, and the output apparatus 12 is structured to receive output signals from the processor apparatus 16. The output apparatus 12 comprises a display 18 that is structured to provide visual output, although other output devices such as speakers, LEDs, tactile output devices, and so forth can be additionally or alternatively used. The output apparatus 12 can also comprise a wireless transceiver 21.

As can be understood from FIG. 1, the input apparatus 8 includes a keypad 24, a touchpad 26 (shown in hidden line drawing in FIG. 1) and a multiple-axis input device which, in the example embodiment depicted herein, is a track ball 32 that will be described, in greater detail below. The keypad 24 comprises a plurality of keys 28 in the example form of a reduced QWERTY keyboard, meaning that at least some of the keys 28 each have a plurality of linguistic elements assigned thereto, with at least some of the linguistic elements being Latin letters arranged generally in a QWERTY configuration. The keys 28 and the track ball 32 all are disposed on the front surface 29 of the housing 6 and serve as input members that are actuatable to provide input to the processor apparatus 16. The keypad 24 and the track ball 32 are advantageously disposed adjacent one another on the front surface 29 of the housing 6. This enables a user to operate the track ball 32 substantially without moving the user's hands away from the keypad 24 during a text entry operation or other operation.

One of the keys 28 is an <ESCAPE> key 31 which, when actuated, provides to the processor apparatus 16 an input that undoes the action which resulted from the immediately preceding input and/or moves the user to a position logically higher within a logical menu tree managed by a graphical user interface (GUI) routine 46. The function provided by the <ESCAPE> key 31 can be used at any logical location within any portion of the logical menu tree except, perhaps, at a conventional home screen (not shown). The <ESCAPE> key 31 is advantageously disposed adjacent the track ball 32 thereby enabling, for example, an unintended or incorrect input from the track ball 32 to be quickly undone, i.e., reversed, by an actuation of the adjacent <ESCAPE> key 31.

Another of the keys 28 is a <MENU> key 33 which, when actuated, provides to the processor apparatus 16 an input that causes the GUI 46 to generate and output on the display 18 a menu (not shown).

While in the depicted example embodiment the multiple-axis input device is the track ball 32, it is noted that multiple-axis input devices other than the track ball 32 can be employed without departing from the disclosed and claimed concept. For instance, other appropriate multiple-axis input devices could include mechanical devices such as joysticks and the like and/or non-mechanical devices such as touch pads, track pads and the like and/or other devices which detect motion or input in other fashions, such as through the use of optical sensors or piezoelectric crystals.

The track ball 32 is freely rotatable in all directions with respect to the housing 6. A rotation of the track ball 32 a predetermined rotational distance with respect to the housing 6 provides an input to the processor apparatus 16, and such inputs can be employed by a number of routines, for example, as navigational inputs, scrolling inputs, selection inputs, and other inputs.

For instance, and as can be seen in FIG. 1, the track ball 32 is rotatable about a horizontal axis 34A to provide vertical scrolling, navigational, selection, or other inputs. Similarly, the track ball 32 is rotatable about a vertical axis 34B to provide horizontal scrolling, navigational, selection, or other inputs. Since the track ball 32 is freely rotatable with respect to the housing 6, the track ball 32 is additionally rotatable about any other axis (not expressly depicted herein) that lies within the plane of the page of FIG. 1 or that extends out of the plane of the page of FIG. 1.

The track ball 32 can be said to be a multiple-axis input device because it provides scrolling, navigational, selection, and other inputs in a plurality of directions or with respect to a plurality of axes, such as providing inputs in both the vertical and the horizontal directions. It is reiterated that the track ball 32 is merely one of many multiple-axis input devices that could be employed on the handheld electronic device 4. As such, mechanical alternatives to the track ball 32, such as a joystick, might have a limited rotation with respect to the housing 6, and non-mechanical alternatives might be immovable with respect to the housing 6, yet all are capable of providing input in a plurality of directions and/or along a plurality of axes.

The track ball 32 additionally is translatable toward the housing 6, i.e., into the plane of the page of FIG. 1, to provide additional inputs. The track ball 32 could be translated in such a fashion by, for example, a user applying an actuating force to the track ball 32 in a direction toward the housing 6, such as by pressing an the track ball 32. The inputs that are provided to the processor apparatus 16 as a result of a translation of the track ball 32 in the indicated fashion can be employed by the routines, for example, as selection inputs, delimiter inputs, or other inputs.

As can be seen in FIG. 1A, the processor apparatus 16 comprises a processor 17 and a memory 20. The processor 17 may be, for instance and without limitation, a microprocessor (µP) that is responsive to inputs from the input apparatus 8 and that provides output signals to the output apparatus 12. The processor 17 interfaces with the memory 20.

The memory 20 can be said to constitute a machine-readable medium and can be any one or more of a variety of types of internal and/or external storage media such as, without limitation, RAM, ROM, EPROM(s), EEPROM(s), FLASH, and the like that provide a storage register for data storage such as in the fashion of an internal storage area of a computer, and can be volatile memory or nonvolatile memory. The memory 20 has stored therein the aforementioned number of routines 22 which are executable on the processor 17. The routines 22 can be in any of a variety of forms such as, without limitation, software, firmware, and the like. Some non-limiting example routines include personal information routines 42, a spell checking routine 44, a disambiguation routine 45, the aforementioned GUI 46, a diacritic selection routine 50, as well as other routines.

Figure 2:
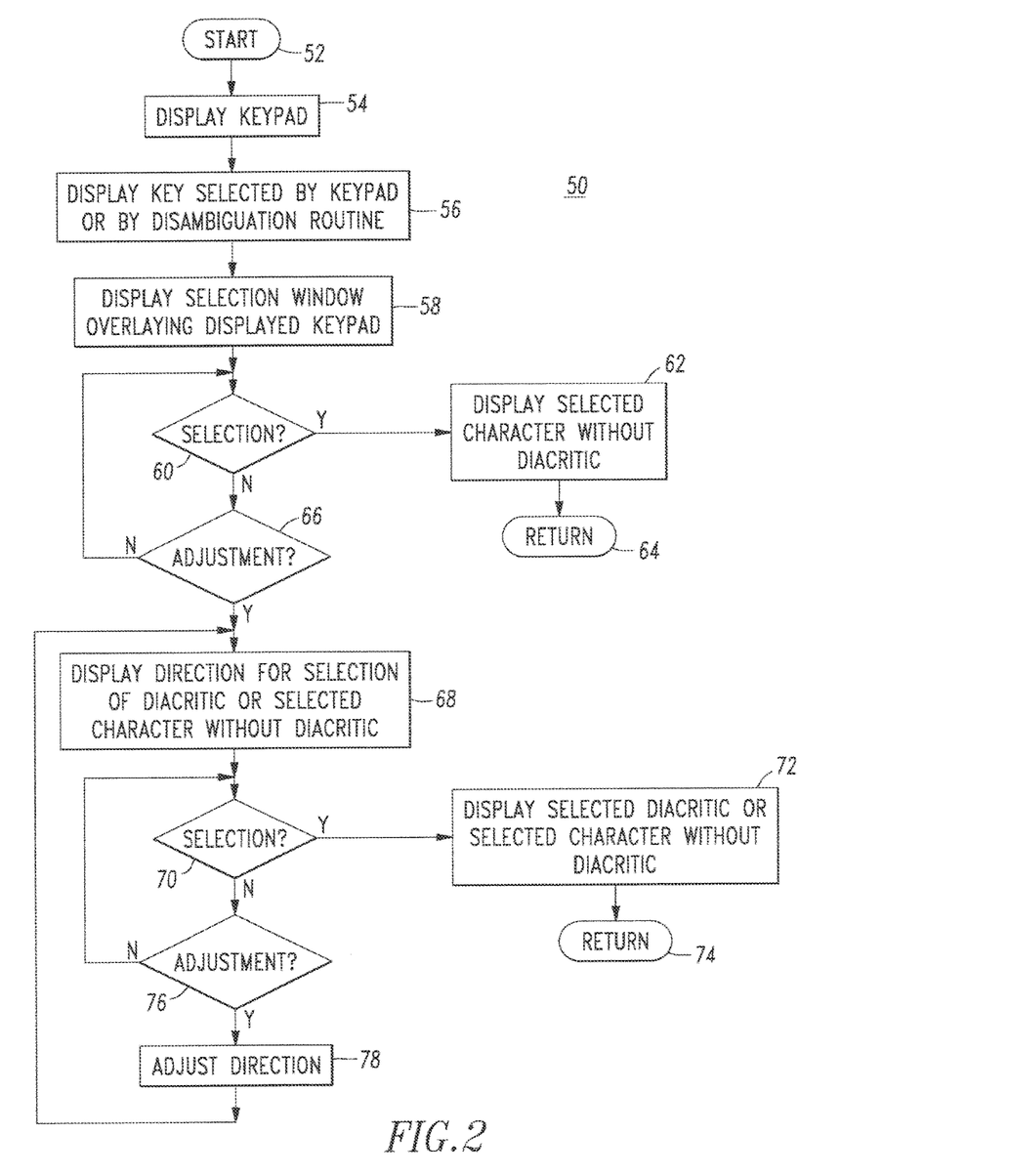
FIG. 2 is a flowchart of a routine of the processor of the handheld electronic device of FIG. 1A for display and selection of a diacritic.

Referring to FIG. 2, the diacritic selection routine 50 for the processor 17 of FIG. 1A is shown. After starting, at 52, the routine 50 displays a representation of a keypad (e.g., a portion of a full keypad or a portion of a reduced keypad), at 54, and displays a representation of a key selected by the keypad or by the disambiguation routine 45, at 56. Next, at 58, a selection window is displayed, which selection window overlays the displayed portion of the keypad. Then, at 60, it is determined if a selection has been made (e.g., by detecting pressing of the track ball 32 of FIG. 1). If so, then at 62, the selected character without the diacritic is displayed before the routine 50 returns, at 64. Otherwise, at 66, it is determined if an adjustment has been made for a diacritic (e.g., by detecting rotation of the track ball 32 about the axis 34B of FIG. 1). If not, then step 60 is repeated. On the other hand, if the direction for selection was adjusted, then, at 68, a representation of that direction is displayed for possible selection of a diacritic or the character without a diacritic.

Next, at 70, it is determined if a selection has been made (e.g., by detecting pressing of the track ball 32). If so, then at 72, the selected diacritic or the selected character without the diacritic is displayed before the routine 50 returns, at 74. Otherwise, at 76, it is determined if an adjustment has been made for a diacritic (e.g., by detecting rotation of the track ball 32 about the axis 34B of FIG. 1). If not, then step 70 is repeated. On the other hand, if an adjustment was made, then, at 78, the direction for selection is adjusted and, at 68, the representation of that direction is displayed for possible selection of another diacritic or the character without a diacritic.

In the example of FIG. 1, the handheld electronic device 4 includes the example reduced keypad 24 having the keys 28 and a selection member, such as the example track ball 32. There, the processor 17 (FIG. 1A) is structured to cooperate with the keypad 24 and the display 18 to display a first representation 100 of a plurality of the keys 28, and a second representation 102 of an activated one of the keys 28, as is shown in FIG. 1. In this instance, since the key 28 ("ER") includes the letters "E" and "R", the processor 17 has caused (e.g., by using the disambiguation routine 45) the letter "E" of the first representation 100 to be highlighted as the second representation 102. Although the reduced keypad 24 is shown, the disclosed and claimed, concept is also applicable to a full keypad as will be discussed, below, in connection with FIGS. 3A-3E and FIGS. 4A-4E.

Referring to FIGS. 3A-3E, a portion of the display 18' of another handheld electronic device 4' having a full keypad 24' is shown. Other than the full keypad 24', the device 4' can be the same as or similar to the device 4 of FIG. 1. For example, the device 4' includes the processor 17 of FIG. 1A. In this example, the processor 17 includes the routine 50 (FIG. 2) and cooperates with the full keypad 24' and the display 18' to display a first representation 104 of a plurality of the plurality of keys 106 of the full keypad 24', a second representation 108 (FIG. 3B) of an activated one of the plurality of keys 106, a third representation 110 (FIG. 3C) including a plurality of diacritics 112 disposed about the second representation 108, and a fourth representation 114 (FIG. 3D) of a direction of selection between the second representation 108 and one of the diacritics 112 of the third representation 110. The processor 17 also cooperates with the example track ball 32 (FIG. 1) or any suitable selection member to adjust (e.g., rotation of the track ball 32 about the axis 343 (FIG. 1) causes a corresponding rotation of the representation 114 to the position shown by the representation 114' (shown in phantom line drawing)) the fourth representation 114 and its direction of selection of one of the diacritics 112. The processor 17 also cooperates with the example track ball 32 (e.g., which can be pressed into the plane of FIG. 1) to select one of the diacritics 112 (e.g., 116 ("é") (FIG. 3E)) for display by the display 18'.

EXAMPLE 1

Alternatively, for example, if the track ball 32 is pressed into the plane of FIG. 1 before being rotated, or if the representations 114 or 114' do not point to one of the diacritics 112, then the letter "e" (FIG. 3B) is selected.

EXAMPLE 2

In this example, the second representation 108 is of an activated one of the keys 106 and includes one character (e.g., the example letter "e"). The third representation 110 of FIGS. 3C and 3D is a selection window having a circular shape displayed on the display 18'. The example selection window includes a representation of a portion of the keypad 24' or a touchpad as the first representation 104, the second representation 108, and the fourth representation 114. A number of the diacritics 112 are accented characters (e.g., "è", "é", "ê" and "ë"). The example selection window (FIGS. 3C and 3D) is a circular selection window having a center 118 and a circular edge 120. The second representation 108 is disposed at about the center 118 of the circular selection window, and each of the diacritics 112 is disposed. at a different position proximate the circular edge 120. The fourth representation 114 is disposed between the center 118 of the circular selection window and the selected one of the diacritics 112. This fourth representation 114 provides a direction of selection or spatial reference corresponding to the selected one of the diacritics 112 (e.g., 116 ("é") of FIG. 3E).

EXAMPLE 3

As one example of the diacritics 112, the disclosed and claimed concept is applicable to accented characters. However, it will be understood that any suitable diacritical character can be employed.

EXAMPLE 4

In addition to the diacritics 112, the disclosed and claimed concept is applicable to other suitable marks, each of which has a suitable logical connection to an initial character. Some non-limiting examples include: (1) the "dollar" symbol "$"

can be under or about the letter "s"; (2) the registration symbol "®" can be under or about the letter "r"; (3) the copyright symbol "©" 122 (FIG. 4C) can be under or about (as shown in FIG. 4C) the letter "c" 124; (4) the Euro symbol "€" can be under or about the letter "e"; (5) the "and" symbol "&" can be under or about the letter "a"; and (6) the at symbol "@" can be under or about the letter "a".

EXAMPLE 5

Figure 3A:
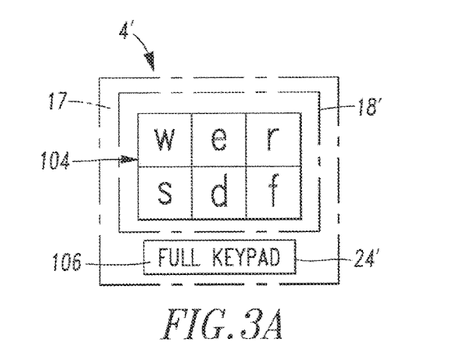
FIGS. 3A-3E, 4A-4E, 5, 6 and 7 are simplified displays of a handheld electronic device for display and selection of a diacritic in accordance with other embodiments of the disclosed and claimed concept.
Figure 3B:
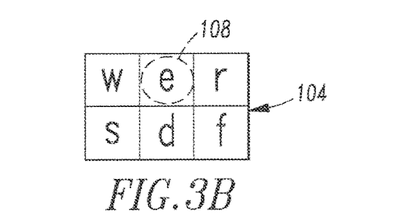
Figure 3C:
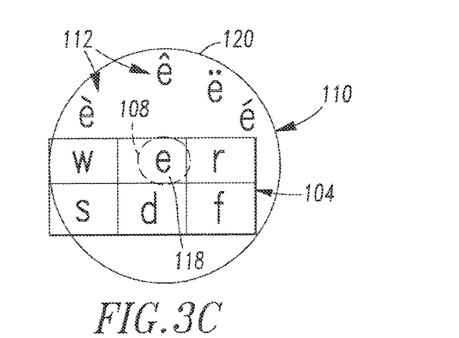
Figure 3D:
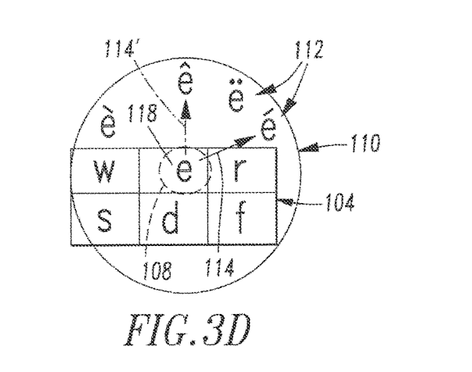
Figure 4A:
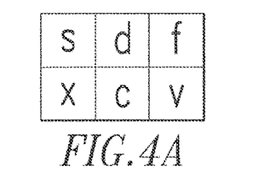
Figure 4B:
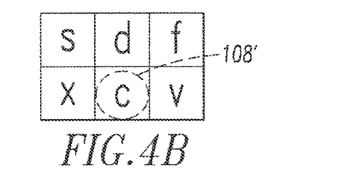
Figure 4C:
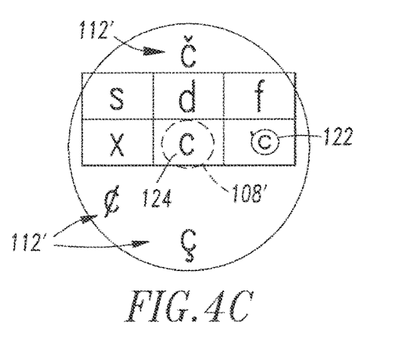
Figure 4D:
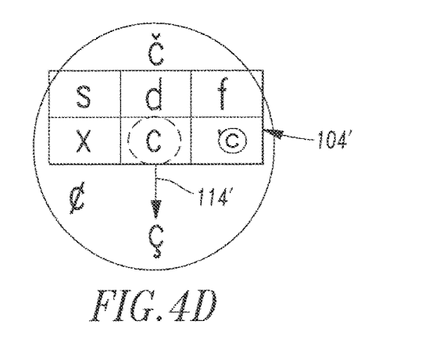

As shown in FIGS. 3D and 4D, by providing a selection window including the representation 104,104' (e.g., an image) of a portion of the keypad 24' or touchpad, along with a designation provided by the representation 108,108' (e.g., a shadow) of the selected character (e.g., "e" or "c"), the directionality of the selected one of the diacritics 112 (mark) preferably corresponds to the direction of selection by the representation 114,114'. This will be further explained, below, in connection with Examples 6 and 7.

EXAMPLE 6

As shown in FIGS. 3C and 3D, for example, the example selection window preferably provides logical directional and/or spatial references that are relatively easy for users to remember. For example, the letter "e" with a forward leaning (or acute) accent, thus, "é", is placed above and to the right on about a 45 degree angle from the start point (e.g., at 108) while the letter "e" with a reverse leaning (or grave) accent, thus, is placed above and to the left on about a 45 degree angle from the start point. Also, the letter "ê" (e.g., having an upper circumflex or hacek) is placed above the start point. However, not all characters and accents need to have a logical placement. See, for example, the letter "ë" or any suitable character having, for example, an upper tilde, umlaut, dieresis, or diaeresis.

EXAMPLE 7

As shown in FIGS. 4C and 4D, for example, the example selection window display preferably provides logical directional and/or spatial references that are relatively easy for users to remember. For example, the letter "č" (e.g., having an upper diacritic) is placed above the start point, while the letter "ç" (e.g., having a lower diacritic) is placed below the start point. Also the symbol "¢" (e.g., having a forward slash) is placed below and to the left on about a 45 degree angle from the start point. However, not all characters and accents need to have a logical placement. See, for example, the symbol "©" 122.

EXAMPLE 8

Although the disclosed and claimed concept deals with diacritical marks 112,112', the disclosed and claimed concept can be applied to the selection of various currency marks (e.g., without limitation, "$"; "€") or punctuation marks (e.g., without limitation, Spanish punctuation marks, such as "¡"; "¿").

EXAMPLE 9

As shown in connection with FIG. 3A, the example input component includes the full keypad 24'. The second representation 108,108' of an activated one of the keys 106 of the keypad 24' is one character (e.g., "e" or "c", as shown).

EXAMPLE 10

Figure 5:
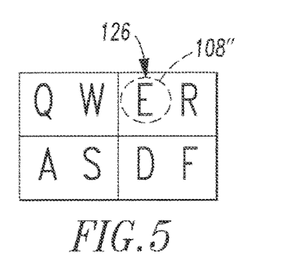
Figure 6:
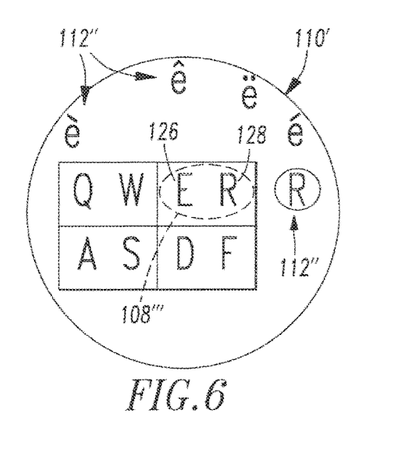

As shown in connection with FIGS. 1, 5 and 6, the input component includes the reduced keypad 24 (FIG. 1). The second representation 108",108' of an activated one of the keys 28 of the keypad 24 is either one character 126 (e.g., "e"), as shown in FIG. 5 and as is obtained from the disambiguation routine 45 (FIG. 1A), or a plurality of characters 126,128 (e.g., "e" and "r"), as shown in FIG. 6. In the example of FIG. 5, the representation 110 of the selection window (FIG. 3C) can be employed. In the example of FIG. 6, the diacritics 112" in the representation 110' of the selection window include, for example, "è", "ê", "ë", "é", and "®".

EXAMPLE 11

As an alternative, in FIG. 2, the step of displaying a representation of a key selected by the keypad or by the disambiguation routine 45, at 56, and the step, at 58, of displaying a selection window, which overlays the displayed portion of the keypad can be combined, such that the displays of FIG. 3B or 4B are not required. In other words, following the display of FIG. 3A, the display of FIG. 3C can be displayed to include a representation including a plurality of diacritics 112 disposed about an activated one of the keys 106 of the keypad 24', or following the display of FIG. 4A, the display of FIG. 4C can be displayed to include a representation including a plurality of diacritics 112' disposed about an activated one of the keys 106 of the keypad 24'.

EXAMPLE 12

As an alternative to Example 11, the displays of FIGS. 3B-3C or FIGS. 4B-4C are not required. In other words, following the display of FIG. 3A, the display of FIG. 3D can be displayed to include a representation including a plurality of diacritics 112 disposed about an activated one of the keys 106 of the keypad 24', and a direction of selection 114' between the activated one of the keys 106 of the keypad 24' and one of the diacritics 112; or following the display of FIG. 4A, the display of FIG. 4D can be displayed to include a representation including a plurality of diacritics 112' disposed about an activated one of the keys 106 of the keypad 24', and a direction of selection 114' between the activated one of the keys 106 of the keypad 24' and one of the diacritics 112'.

EXAMPLE 13

Figure 3E:
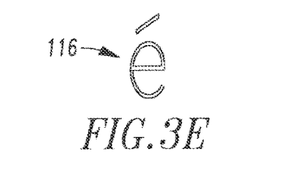
Figure 4E:
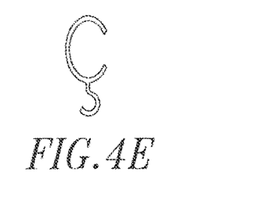

Although the examples of FIGS. 2, 3A-3E arid 4A-4E have been described in connection with the keypads 24,24' and the track ball 32, operation with the touchpad 26 (FIG. 1) is also possible. For example, if a user places his/her finger on the touchpad 26, then the processor apparatus 16 (FIG. 1) can detect this and responsively cause a change of the display of the device 4,4' from FIG. 3B to FIG. 3C or 3D. This visual cue can allow the user to move his/her linger in any direction in the two-dimensional plane of the touchpad 26. For example, the X_Finger and Y_Finger directions of the touchpad 26 can be tracked by the processor apparatus 16 to determine a direction of motion, in order to select (e.g., without limitation, by rotating one of the representations 114, 114') one of the diacritics 112,112' (e.g., as shown in FIG. 3E or 4E) upon removal of the user's finger from the touchpad 26.

EXAMPLE 14

As an alternative to Example 13, in FIG. 3B or 4B, the user can touch the touchpad 26 (FIG. 1) at a position, for example, shown in at 108 of FIG. 3B or 108' of FIG. 3B. In response, the processor apparatus 16 causes a change to the display of the device 4,4' from FIG. 3B to FIG. 3C or 3D or from FIG. 4B to FIG. 4C or 4D. Since the diacritics 112,112' are displayed with an offset from the point of touch, they are visible. Then, the user moves the point of touch (e.g., by moving his/her finger in any direction in the two-dimensional plane of the touchpad 26) from 108,108' to a desired one of the diacritics 112,112'. The processor apparatus 16 can optionally cause a change to the display of the device 4,4' during this movement, in order to show the current point of touch. Then, after the point of touch is placed over the intended one of the diacritics 112,112' a release or an increase in pressure of the touchpad 26 can be detected by the processor apparatus 16 in order to select one of the diacritics 112,112' for display at FIG. 3E or 4E.

EXAMPLE 15

Figure 7:
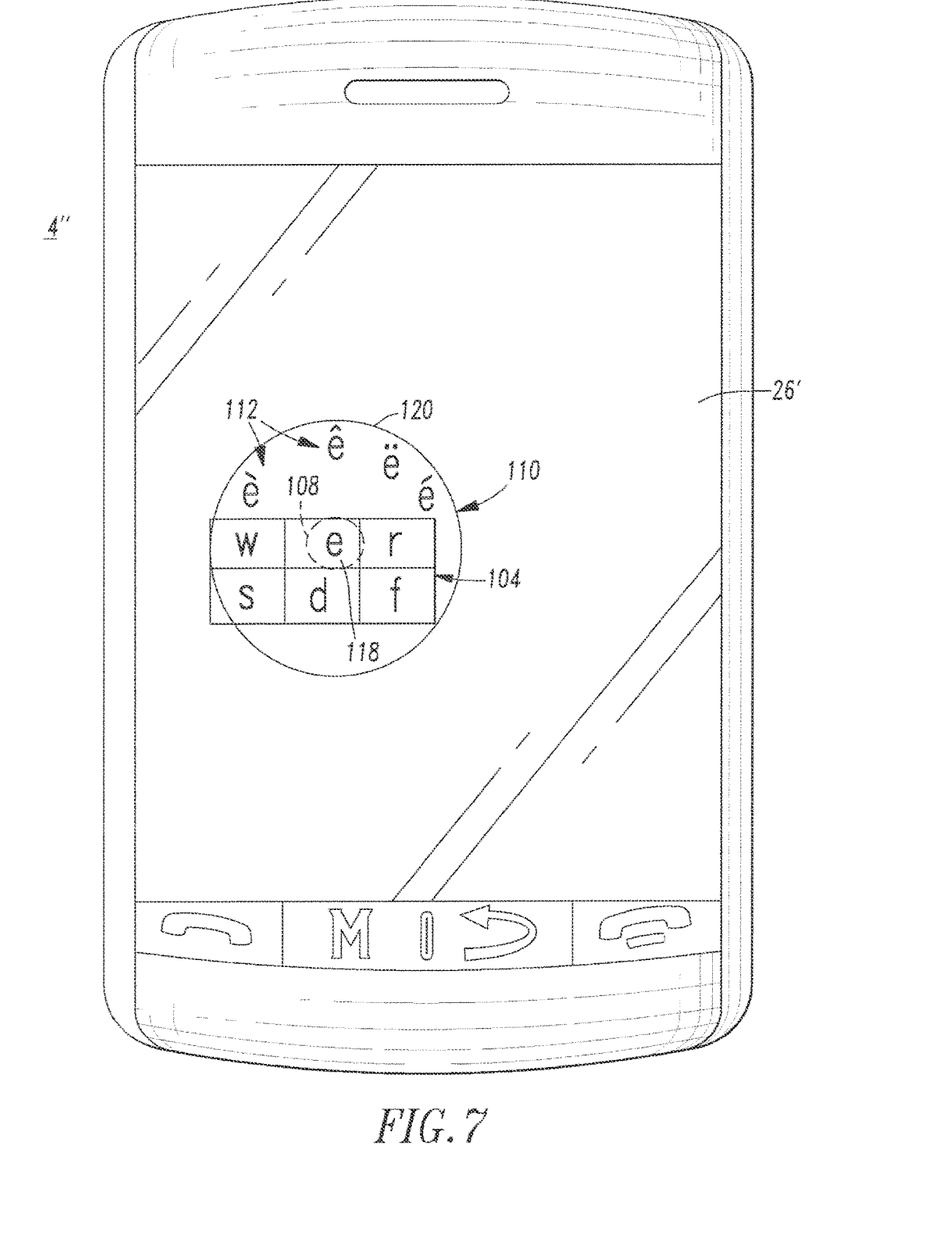

As an alternative to Examples 13 and 14, as shown in FIG. 7, the user can touch another type of touchpad, such as the touchscreen 26' of handheld electronic device 4".

Although the disclosed and claimed concept is disclosed in connection with a handheld electronic device including a track ball and a touchpad as part of its use interface, it will be appreciated that the disclosed and claimed concept can be employed in connection with a wide range of user interfaces, including, for example and without limitation, any one, some or all of a touchscreen, touchpad, keyboard, keypad, track ball and other input and output apparatus.

While specific embodiments of the disclosed and claimed concept have been described in detail, it will be appreciated by those skilled in the art that various modifications and alternatives to those details could be developed in light of the overall teachings of the disclosure. Accordingly, the particular arrangements disclosed are meant to be illustrative only and not limiting as to the scope of the disclosed and claimed concept which is to be given the full breadth of the claims appended and any and all equivalents thereof.

What is claimed is:

1. A method for inputting a diacritic to a handheld electronic device, comprising:
receiving a first user input indicative of a character selected by a user via a keyboard of the handheld electronic device;
in response to receiving the first user input, displaying, in a selection window of the handheld electronic device different from the keyboard of the handheld electronic device, a plurality of character keys of the keyboard and a plurality of diacritics corresponding to the selected character, wherein the selected character is a character displayed on a key of the keyboard, the selected character is displayed in the selection window, the plurality of diacritics are displayed, in the selection window, in different locations around the displayed selected character, each diacritic of the plurality of diacritics is displayed in the selection window in a corresponding location around the displayed selected character based on a directional stroke of a diacritical mark of the respective diacritic, and the plurality of diacritics comprise a first character having an upper acute accent located above and to right of the displayed selected character;
receiving a second user input for a preferred selection of one of the diacritics; and
displaying the preferred selection of one of the diacritics in place of the character.

2. The method of claim 1, wherein the selection window has a circular border; and further comprising:
displaying the plurality of character keys at substantially a center of the selection window; and
displaying the plurality of diacritics in different directions proximate the circular border.

3. The method of claim 1, wherein the selection window includes a representation of a portion of a keyboard, the portion of the keyboard including the plurality of character keys corresponding to a plurality of characters, the plurality of characters including the selected character.

4. The method of claim 3, wherein the plurality of diacritics displayed in the selection window include diacritics corresponding to at least two of the plurality of characters represented by the portion of the keyboard.

5. The method of claim 4, wherein the at least two of the plurality of characters correspond to adjacent keys in the portion of the keyboard.

6. The method of claim 1, wherein the plurality of diacritics comprises a second character having an upper grave accent located above and to left of the displayed selected character, and a third character having an upper circumflex or hacek located above the displayed selected character.

7. The method of claim 1, wherein the handheld electronic device includes an input component for receiving user inputs, and the input component is a touch screen.

8. A handheld electronic device comprising:
an input component for receiving user inputs;
a display component for displaying outputs;
a memory for storing instructions; and
a processor for executing the instructions to:
receive a first user input indicative of a character selected by a user via a keyboard of the handheld electronic device;
in response to receiving the first user input, display, in a selection window of the handheld electronic device different from the keyboard of the handheld electronic device, a plurality of character keys of the keyboard and a plurality of diacritics corresponding to the selected character, wherein the selected character is a character displayed on a key of the keyboard, the selected character is displayed in the selection window, the plurality of diacritics are displayed, in the selection window, in different locations around the displayed selected character, each diacritic of the plurality of diacritics is displayed in the selection window in a corresponding location around the displayed selected character based on a directional stroke of a diacritical mark of the respective diacritic, and the plurality of diacritics comprise a first character having an upper acute accent located above and to right of the displayed selected character;
receive a second user input for a preferred selection of one of the diacritics; and
display the preferred selection of one of the diacritics in place of the character.

9. The handheld electronic device of claim 8, wherein the selection window has a circular border; and the processor further for executing the instructions to:
display the plurality of character keys at substantially a center of the selection window; and display the plurality of diacritics in different directions proximate the circular border.

10. The handheld electronic device of claim 8, wherein the selection window includes a representation of a portion of a keyboard, the portion of the keyboard including the plurality of character keys corresponding to a plurality of characters, the plurality of characters including the selected character.

11. The handheld electronic device of claim 10, wherein the plurality of diacritics displayed in the selection window include diacritics corresponding to at least two of the plurality of characters represented by the portion of the keyboard.

12. The handheld electronic device of claim 11, wherein the at least two of the plurality of characters correspond to adjacent keys in the portion of the keyboard.

13. The handheld electronic device of claim 8, wherein the plurality of diacritics comprises a second character having an upper grave accent located above and to left of the displayed selected character, and a third character having an upper circumflex or hacek located above the displayed selected character.

14. The handheld electronic device of claim 8, wherein the handheld electronic device includes an input component for receiving user inputs, and the input component is a touch screen.

15. A tangible, non-transitory computer-readable medium containing instructions which, when executed, cause a handheld electronic device to perform operations comprising:
receiving a first user input indicative of a character selected by a user via a keyboard of the handheld electronic device;
in response to receiving the first user input, displaying, in a selection window of the handheld electronic device different from the keyboard of the handheld electronic device, a plurality of character keys of the keyboard and a plurality of diacritics corresponding to the selected character, wherein the selected character is a character displayed on a key of the keyboard, the selected character is displayed in the selection window, the plurality of diacritics are displayed, in the selection window, in different locations around the displayed selected character, each diacritic of the plurality of diacritics is displayed in the selection window in a corresponding location around the displayed selected character based on a directional stroke of a diacritical mark of the respective diacritic, and the plurality of diacritics comprise a first character having an upper acute accent located above and to right of the displayed selected character;
receiving a second user input for a preferred selection of one of the diacritics; and
displaying the preferred selection of one of the diacritics in place of the character.

16. The tangible, non-transitory computer-readable medium of claim 15, wherein the selection window has a circular border; and the operations further comprising:
displaying the plurality of character keys at substantially a center of the selection window; and
displaying the plurality of diacritics in different directions proximate the circular border.

17. The tangible, non-transitory computer-readable medium of claim 15, wherein the selection window includes a representation of a portion of a keyboard, the portion of the keyboard including the plurality of character keys corresponding to a plurality of characters, the plurality of characters including the selected character.

18. The tangible, non-transitory computer-readable medium of claim 17, wherein the plurality of diacritics displayed in the selection window include diacritics corresponding to at least two of the plurality of characters represented by the portion of the keyboard.

19. The tangible, non-transitory computer-readable medium of claim 18, wherein the at least two of the plurality of characters correspond to adjacent keys in the portion of the keyboard.

20. The tangible, non-transitory computer-readable medium of claim 15, wherein the plurality of diacritics comprises a second character having an upper grave accent located above and to left of the displayed selected character, and a third character having an upper circumflex or hacek located above the displayed selected character.

* * * * *